(12) United States Patent
Rorrer et al.

(10) Patent No.: US 11,174,343 B2
(45) Date of Patent: Nov. 16, 2021

(54) BIODERIVED BIPHENYL-CONTAINING COMPOUNDS AND THEIR CONVERSION TO POLYMERS AND MACROMONOMERS

(71) Applicant: Alliance for Sustainable Energy, LLC, Golden, CO (US)

(72) Inventors: Nicholas Rorrer, Golden, CO (US); Gregg Tyler Beckham, Golden, CO (US); Caroline Bradshaw Hoyt, Denver, CO (US); Jared Jon Anderson, Minneapolis, MN (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 64 days.

(21) Appl. No.: 16/791,873

(22) Filed: Feb. 14, 2020

(65) Prior Publication Data
US 2020/0262972 A1    Aug. 20, 2020

Related U.S. Application Data

(60) Provisional application No. 62/805,448, filed on Feb. 14, 2019.

(51) Int. Cl.
| | |
|---|---|
| *C08G 63/66* | (2006.01) |
| *C07C 69/017* | (2006.01) |
| *C08G 63/00* | (2006.01) |

(52) U.S. Cl.
CPC ............ *C08G 63/66* (2013.01); *C07C 69/017* (2013.01); *C08G 63/00* (2013.01)

(58) Field of Classification Search
USPC .......................... 528/219, 190, 193, 194, 286
See application file for complete search history.

(56) References Cited

U.S. PATENT DOCUMENTS

| | | | |
|---|---|---|---|
| 4,737,313 A | 4/1988 | Saito et al. | |
| 10,774,030 B2* | 9/2020 | Bolikal | C08G 64/06 |
| 2017/0060008 A1 | 3/2017 | Okuda et al. | |
| 2020/0181321 A1* | 6/2020 | Kohn | A61K 47/34 |

FOREIGN PATENT DOCUMENTS

| | | |
|---|---|---|
| JP | 2017-210569 A | 11/2017 |
| WO | 2010/048067 A2 | 4/2010 |
| WO | 2018/067181 A1 | 4/2018 |

OTHER PUBLICATIONS

Colquhoun et al., An Aromatic Plyether in Which Sequence-Randomization Leads to Induction of Crystallinity: X-ray Structure of the Crystalline Phase [-OArCOArArCOAr-]n (Ar=1,4-Phenylene), Macromolecules, 1993, vol. 26, pp. 107-111.

Gindt et al., "Nanoporous polysulfone membranes via a degradable block copolymer precursor for redox flow batteries", Journal of Materials Chemistry A, 2016, vol. 4, pp. 4288-4295.

\* cited by examiner

*Primary Examiner* — Terressa Boykin
(74) *Attorney, Agent, or Firm* — Michael A. McIntyre

(57) ABSTRACT

The present disclosure relates to a composition that includes

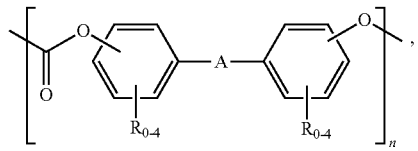

where A includes at least one of a carbon-carbon bond or a bridging group, R includes between 0 and 4 of a first hydrocarbon, and n is between 2 and 3,000. In some embodiments of the present disclosure, the bridging group may include a linear hydrocarbon chain and/or a branched hydrocarbon chain. In some embodiments of the present disclosure, the bridging group may include between 1 and 10 carbon atoms.

19 Claims, 4 Drawing Sheets

Figure 3

BIODERIVED BIPHENYL-CONTAINING COMPOUNDS AND THEIR CONVERSION TO POLYMERS AND MACROMONOMERS

CROSS-REFERENCE TO RELATED APPLICATIONS

This application claims priority from U.S. Provisional Patent Application No. 62/805,448 filed Feb. 14, 2019, the disclosure of which is incorporated herein by reference in its entirety.

CONTRACTUAL ORIGIN

This invention was made with government support under Contract No. DE-AC36-08GO28308 awarded by the Department of Energy. The government has certain rights in the invention.

SUMMARY

An aspect of the present disclosure is a composition that includes

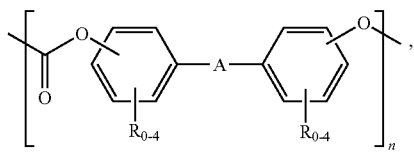

where A includes at least one of a carbon-carbon bond or a bridging group, R includes between 0 and 4 of a first hydrocarbon, and n is between 2 and 3,000.

In some embodiments of the present disclosure, the bridging group may include a linear hydrocarbon chain and/or a branched hydrocarbon chain. In some embodiments of the present disclosure, the bridging group may include between 1 and 10 carbon atoms.

In some embodiments of the present disclosure, the bridging group may be saturated. In some embodiments of the present disclosure, the bridging group may be unsaturated. In some embodiments of the present disclosure, the bridging group may further include at least one of an oxygen atom, a sulfur atom, a nitrogen atom, and/or a phosphorus atom. In some embodiments of the present disclosure, the bridging group may further include at least one of an alcohol, a carboxylic acid, a methoxy group, an ether, and/or a furan.

In some embodiments of the present disclosure, the R may include a linear hydrocarbon chain and/or a branched hydrocarbon chain. In some embodiments of the present disclosure, R may include between 1 and 10 carbon atoms. In some embodiments of the present disclosure, R may be saturated. In some embodiments of the present disclosure, R may be unsaturated. In some embodiments of the present disclosure, R may further include at least one of an oxygen atom, a sulfur atom, a nitrogen atom, and/or a phosphorus atom. In some embodiments of the present disclosure, R may further include at least one of an alcohol, a carboxylic acid, a methoxy group, an ether, an aromatic, and/or a furan. In some embodiments of the present disclosure, A and R may be derived from a biphenyl diol. In some embodiments of the present disclosure, the biphenyl diol may be bioderived.

An aspect of the present disclosure is a composition that includes

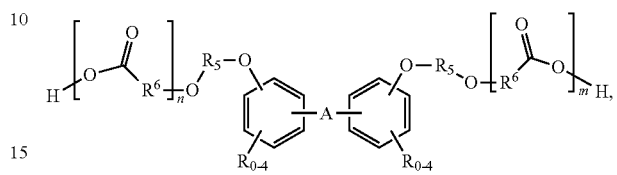

where A includes at least one of a carbon-carbon bond or a bridging group, R includes between 0 and 4 of a first hydrocarbon, $R_1$ includes a second hydrocarbon, $R_2$ includes a third hydrocarbon, n is between 2 and 3,000, and m is between 2 and 3,000.

An aspect of the present disclosure is a composition that includes

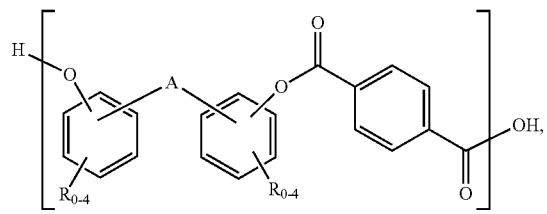

where A includes at least one of a carbon-carbon bond or a bridging group, R includes between 0 and 4 of a first hydrocarbon, $R_5$ includes a second hydrocarbon, $R_6$ includes a third hydrocarbon, n is between 2 and 2,000, and m is between 2 and 2,000.

An aspect of the present disclosure is a composition that includes

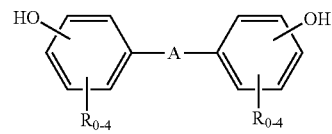

where A includes at least one of a carbon-carbon bond or a bridging group, R includes between 0 and 4 of a first hydrocarbon, and n is between 2 and 3,000.

An aspect of the present disclosure is a method that includes a first reacting of

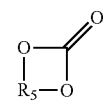

with

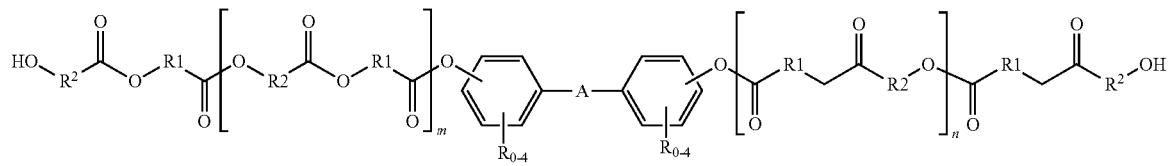

to produce a first product having a first structure that includes

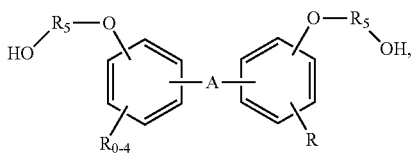

where A includes at least one of a carbon-carbon bond or a bridging group, R includes between 0 and 4 of a first hydrocarbon, and $R_5$ includes a second hydrocarbon. In some embodiments of the present disclosure, the method may further include a second reacting of the first product and

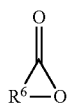

to produce a second product having a second structure that includes

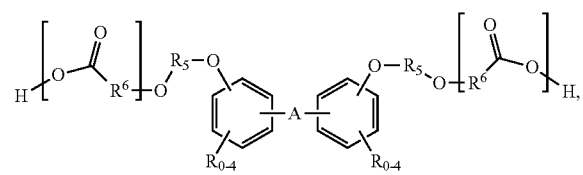

where $R_6$ includes a third hydrocarbon.

BRIEF DESCRIPTION OF THE DRAWINGS

Some embodiments are illustrated in referenced figures of the drawings. It is intended that the embodiments and figures disclosed herein are to be considered illustrative rather than limiting.

FIG. 3 illustrates NMR results showing the successful addition of lactones to alcohol functional groups, according to some embodiments of the present disclosure.

DETAILED DESCRIPTION

Figure 1:
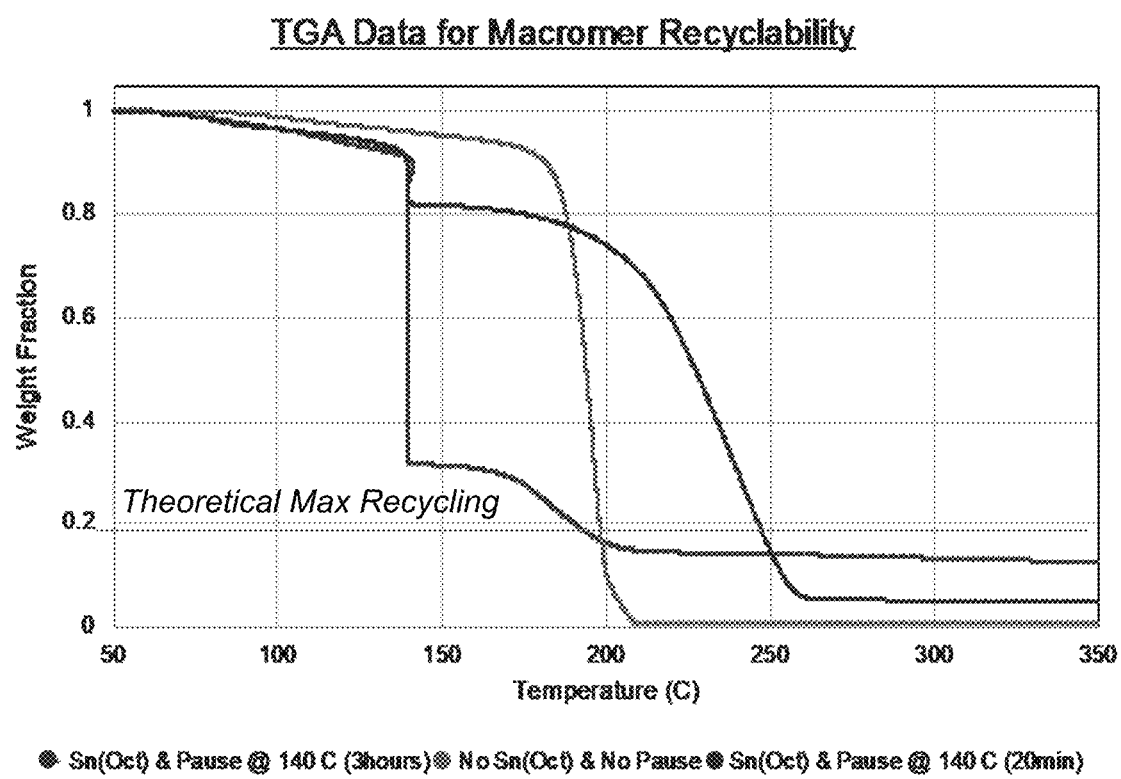
FIG. 1 illustrates thermal degradation results obtained for copolymers, according to some embodiments of the present disclosure.

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure generally relates to the use of biomass derived intermediates to produce useful monomers and polymers, which are similar in structure and function to bisphenol A (BPA) and polycarbonates, respectively. In some embodiments of the present disclosure, it is shown that BPA-like, biphenyl-containing compounds, derived from lignin deconstruction, may be converted to a variety of useful polymers. The general structure of a biphenyl-containing compound, as defined herein, is shown below (Structure 1).

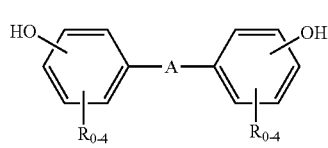

Structure 1

Thus, each benzene ring of Structure 1 has a hydroxyl group attached to it, as well as between zero and four R-groups. A may be any atom or bridging group as defined herein, or A may be only one carbon-carbon bond linking the two adjacent benzene rings. In some embodiments of the present disclosure, bridging group A may include, among other things, at least one of an ether, a furan, a linear alkyl chain, and/or a branched alkyl chain. For the case where the biphenyl structure is absent of R-groups, it simplifies to a biphenyl diol. However, in some embodiments of the present disclosure, the biphenyl structure may contain one or more R-groups. It should be noted, that for cases where the biphenyl structure includes more than one R-group, they may be the same or different. Thus, R may include at least one of an aromatic and/or an alkyl group, a simple hydrocarbon, and/or R may contain other elements including for example, oxygen, nitrogen, phosphorous, and/or sulfur. Examples of alkyl groups include a methyl group, an ethyl group, and/or a butyl group. In some embodiments of the present disclosure, R may include at least one of an unsaturated hydrocarbon (e.g. containing carbon-carbon double and/or triple bonds), an alcohol, a carboxylic acid, a methoxy group, an ether, and/or a furan ring.

Some specific examples of biphenyl diols as defined by generalized Structure 1, according to some embodiments of the present disclosure, are shown below, with BPA shown as a comparison: Structure 2—BPA; Structure 3—[1,1'-biphenyl]-2,2'-diol; Structure 4—[1,1'-biphenyl]-3,3'-diol, 4,4'-dimethoxy-6,6'-dipropyl-. Structures 3 and 4 are bioderived biphenyl diols, and as will be shown, these molecules can provide significant potential benefits to macromonomers and polymers that use them instead of BPA.

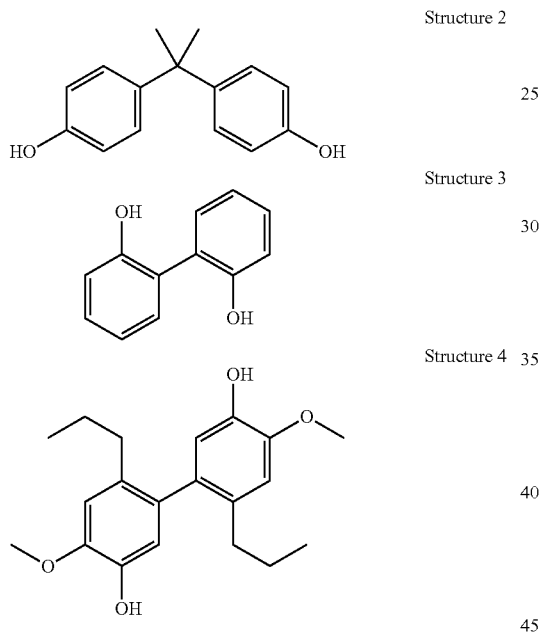

Structure 2

Structure 3

Structure 4

Additional examples of biphenyl diols that are defined by generalized Structure 1 are summarized below in Scheme 1. $R_1$ and $R_2$ may be at least one of a hydroxyl group, a carboxylic acid, and/or a methyl group. The dashed bonds may be saturated or unsaturated bonds (i.e. a carbon-carbon single bond and/or a carbon-carbon double bonds). $R_1$ and $R_2$ may different or the same.

Scheme 1

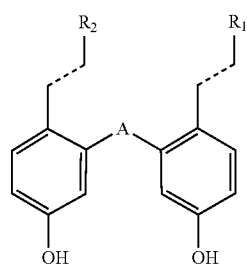

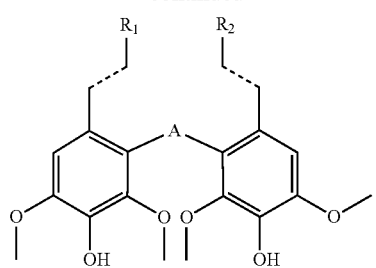

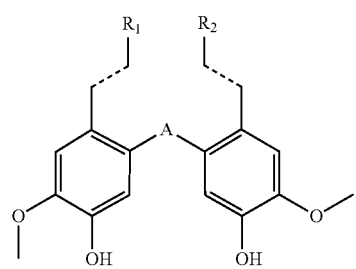

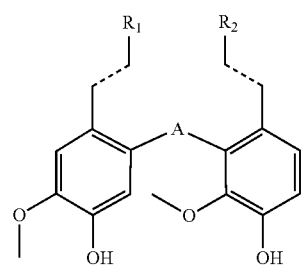

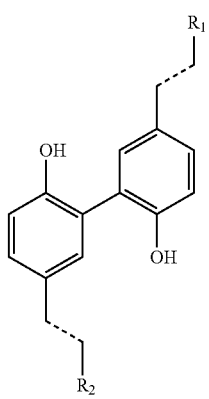

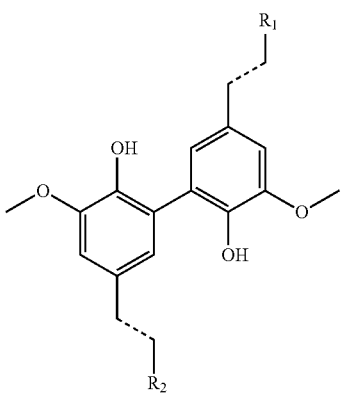

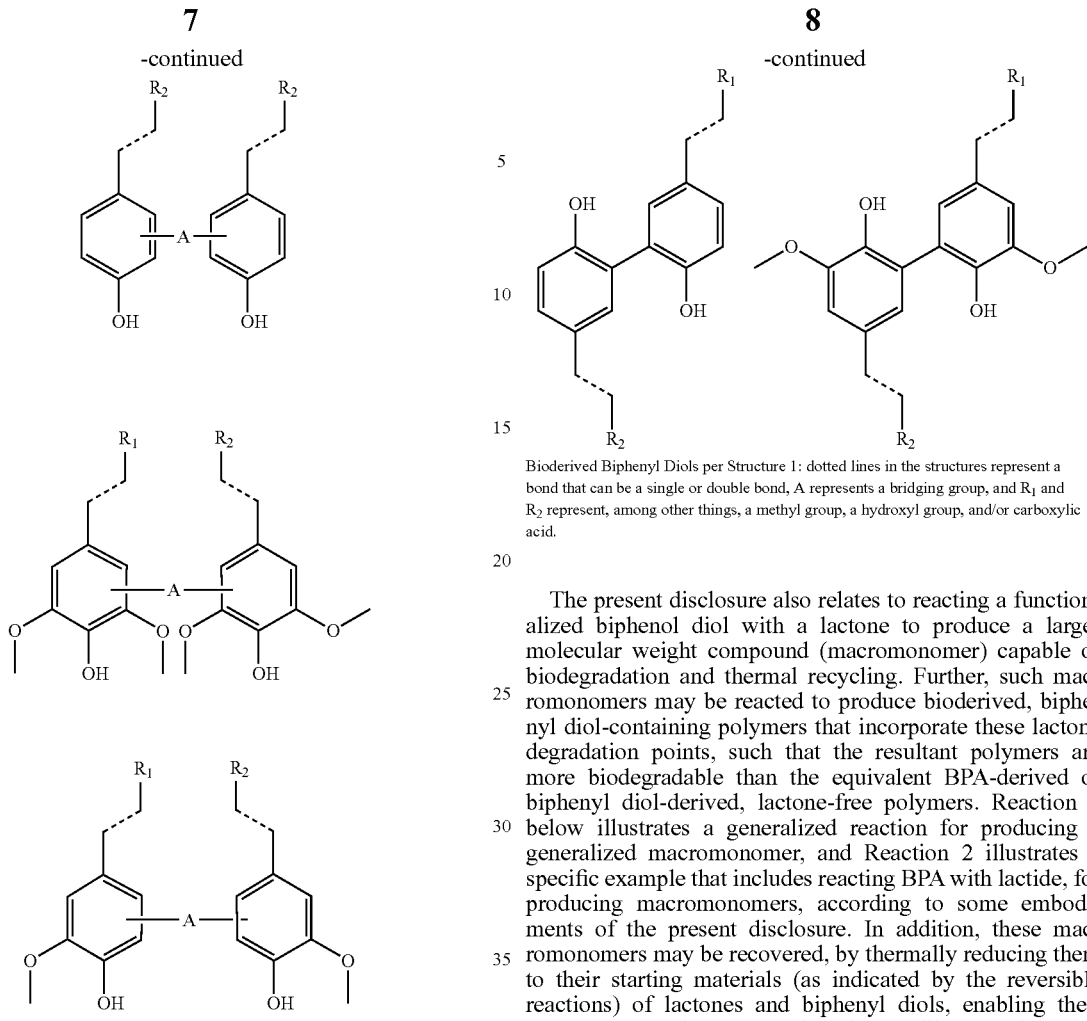

Bioderived Biphenyl Diols per Structure 1: dotted lines in the structures represent a bond that can be a single or double bond, A represents a bridging group, and $R_1$ and $R_2$ represent, among other things, a methyl group, a hydroxyl group, and/or carboxylic acid.

The present disclosure also relates to reacting a functionalized biphenol diol with a lactone to produce a larger molecular weight compound (macromonomer) capable of biodegradation and thermal recycling. Further, such macromonomers may be reacted to produce bioderived, biphenyl diol-containing polymers that incorporate these lactone degradation points, such that the resultant polymers are more biodegradable than the equivalent BPA-derived or biphenyl diol-derived, lactone-free polymers. Reaction 1 below illustrates a generalized reaction for producing a generalized macromonomer, and Reaction 2 illustrates a specific example that includes reacting BPA with lactide, for producing macromonomers, according to some embodiments of the present disclosure. In addition, these macromonomers may be recovered, by thermally reducing them to their starting materials (as indicated by the reversible reactions) of lactones and biphenyl diols, enabling their recovery to produce new polycarbonate-like materials and/or biphenyl-containing materials.

Reaction 1

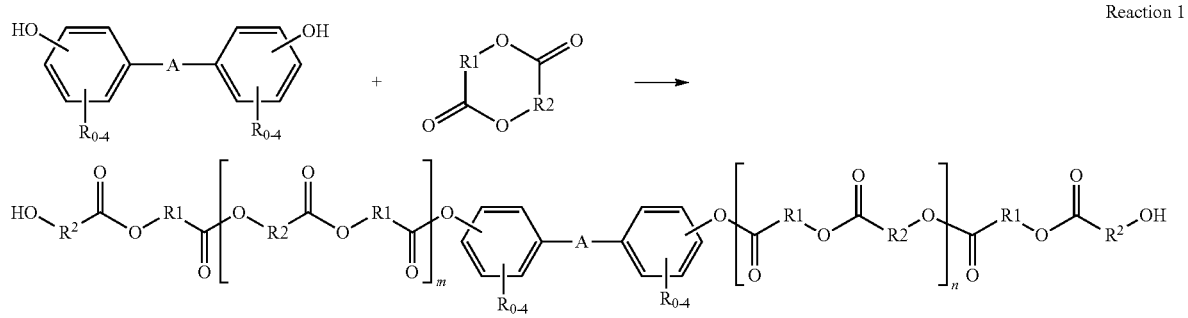

Reaction 2

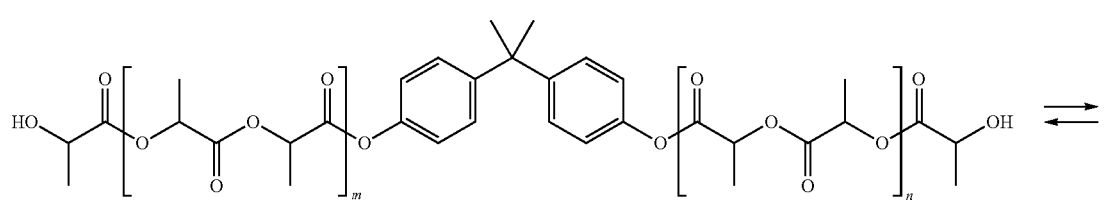

-continued

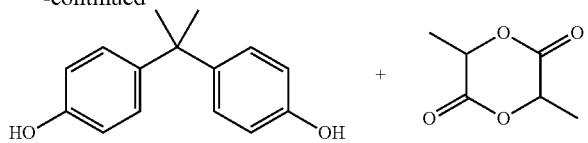

To demonstrate thermal recyclability, thermogravimetric analysis was implemented on the macromonomer and polymers in the presence and absence of a catalyst, specifically stanous(octoate) (also called tin (IV) octoate), which can catalyze the "backbiting"/thermal recycling of lactones to their monomeric form. FIG. 1 illustrates the thermal degradation results obtained for copolymers similar to that shown in Reaction 2. Table 1 summarizes some of the key results in which the weight percent of the lactide and BPA in the macromer are reported. If the lactide was 100% recycled, the weight fraction after the thermal recycling would be 0.197.

TABLE 1

Data for a Three-Hour Hold Experiment - Demonstrates thermo-chemical recycling of a polymer when a catalyst is present. The test was conducted for 3 hours and up to 85% of the theoretical recycling of the lactide of the BPA macromonomer was achieved.

| Measured value | Wt. fraction |
| --- | --- |
| BPA in macromonomer. | 0.197 |
| Lactide in macromonomer. | 0.803 |
| Mass remaining after 140° C. hold. | 0.315 |
| Lactide recycled after 140° C. hold. | 0.853 |

In order to enable greater control of the macromonomer lactide loading and to remove the need for complicated separation steps, the biphenyl diols described herein, as generally described by Structure 1, may initially be functionalized with a cyclic carbonate to convert the hydroxyl groups to primary and/or secondary alcohols, as shown in generalized Reaction 3 below.

Reaction 3

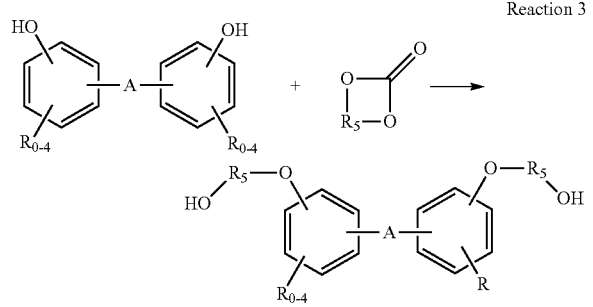

In some embodiments of the present disclosure, for the case when the biphenyl is the 5-5' dimer, the cyclic carbonate is ethylene carbonate, and the catalyst for reaction is an ammonium bromide such as TBAB (tetrabutylammonium bromide) the reaction temperature may be between 60° C. and 180° C., and the reaction time may be between 5 minutes and 5 days. This exemplary reaction is shown below (Reaction 4A).

Reaction 4A

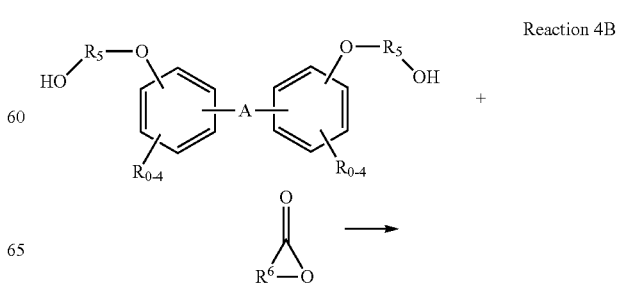

Figure 2:
FIG. 2 illustrates NMR results validating the successful conversion of a biphenyl diol's hydroxyl groups to alcohols, according to some embodiments of the present disclosure.

NMR results obtained from an experiment carrying out Reaction 4A, validating the successful conversion of the biphenyl diol's hydroxyl groups to alcohols are shown in FIG. 2. A generalized form of Reaction 4A is shown in Reaction 4B.

Figure 3:
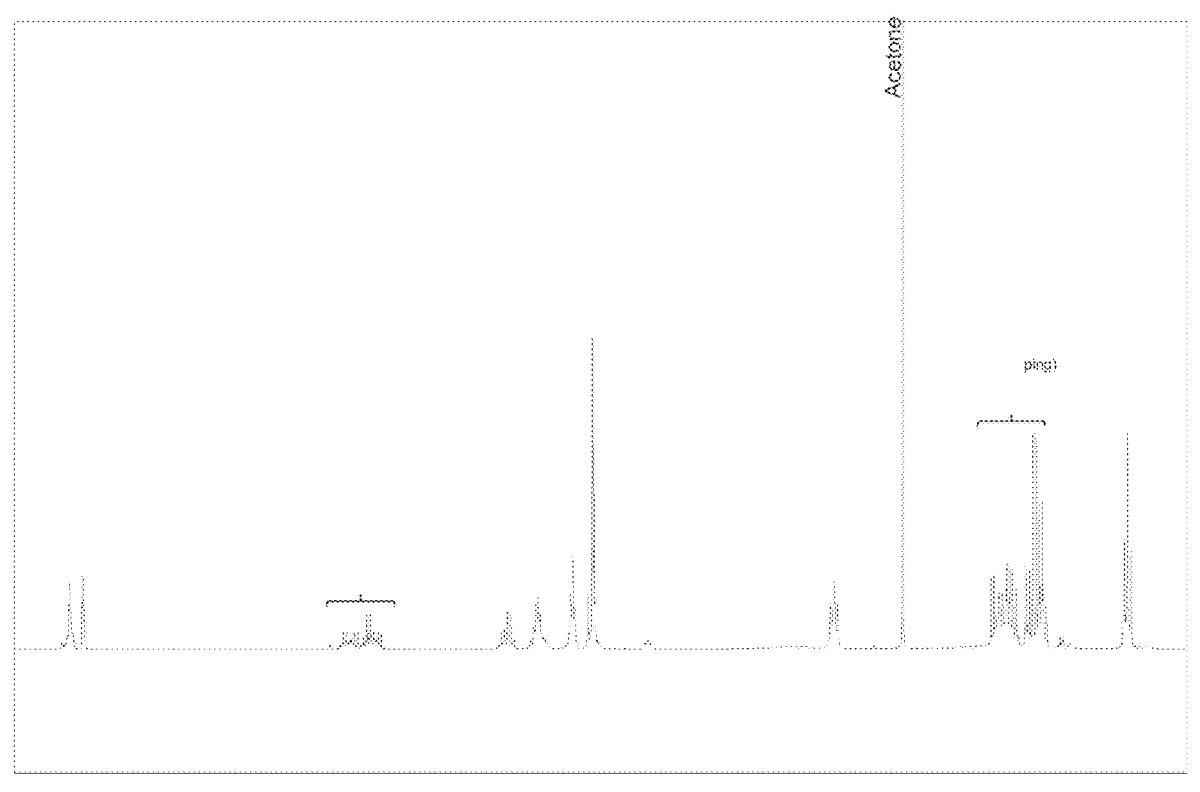

The products of Reaction 3 or Reaction 4A can further be reacted with lactones (Reactions 1 and 2) to enable precise control over their loading. The general structure of the macromonomer may resemble Structure 5. NMR results showing the successful addition of lactones to the alcohol functional groups (product of Reaction 4A) resulting in Structure 5, are shown in FIG. 3.

Reaction 4B

-continued

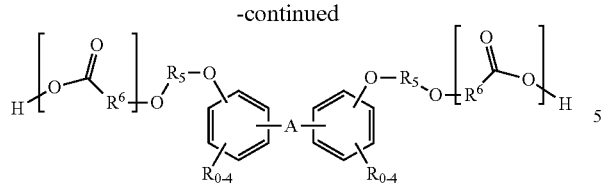

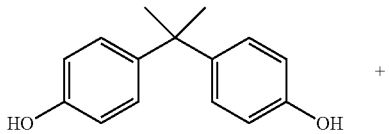

Reaction 5

Structure 5

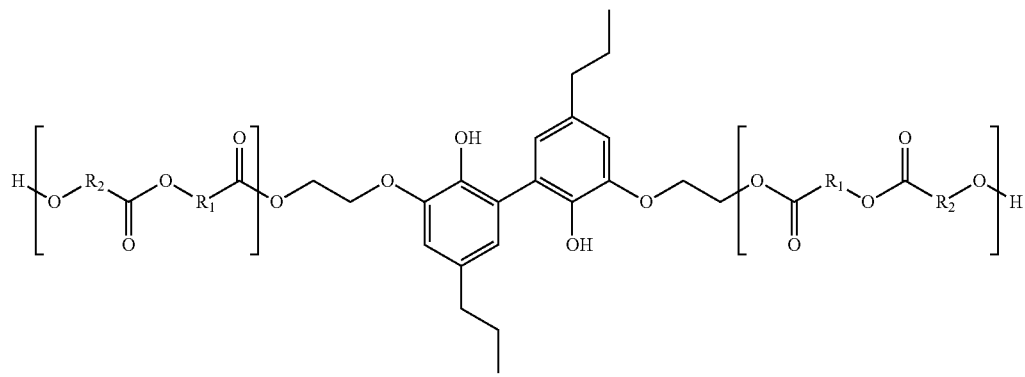

The present disclosure also relates to reacting functionalized biphenol diols, like those represented by generalized Structure 1, and as shown in Scheme 1, to produce novel and useful homopolymers having the general structure shown below (Structure 6).

Structure 6

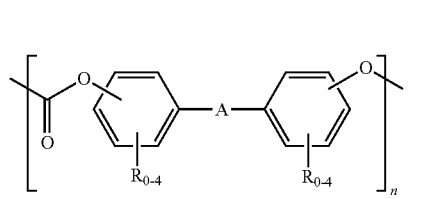

Structure 6 is referred to herein as a homopolymer having a polycarbonate structure. The end groups of Structure 6 may include at least one of a hydroxyl group, an ester group, and/or a halogen (e.g. chlorine, bromine, fluorine, and/or iodine).

Homopolymers having structures like that of Structure 6 may be produced by at least two different reaction routes, the first by reacting a biphenyl diol with a carbonate, and the second by reacting a biphenyl diol with a halogenated carbonyl. Three specific examples of such reactions are provided below: Reaction 5—reacting BPA (Structure 2) to make a BPA homopolymer; Reaction 6—reacting [1,1'-biphenyl]-2,2'-diol (Structure 3) to make its homopolymer; and Reaction 7—reacting [1,1'-biphenyl]-3,3'-diol, 4,4'-dimethoxy-6,6'-dipropyl- (Structure 4) to make its homopolymer. Although Reactions 5-7 illustrate chlorine as an end group, any other halogen may be used as well (e.g. chlorine, bromine, fluorine, and/or iodine). In addition, although not shown, various polymers may be synthesized by reacting more than one biphenyl diol with at least one of a carbonate and/or halogenated carbonyl. The R end group shown in these reactions may be a hydrogen atom and/or a hydrocarbon chain.

-continued

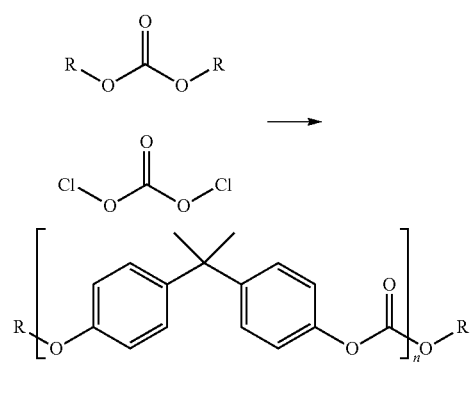

Reaction 6

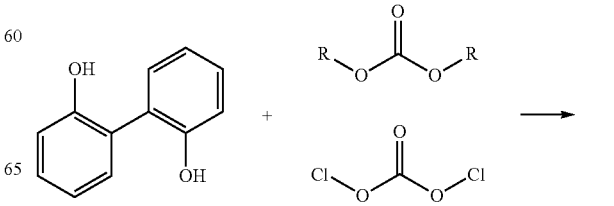

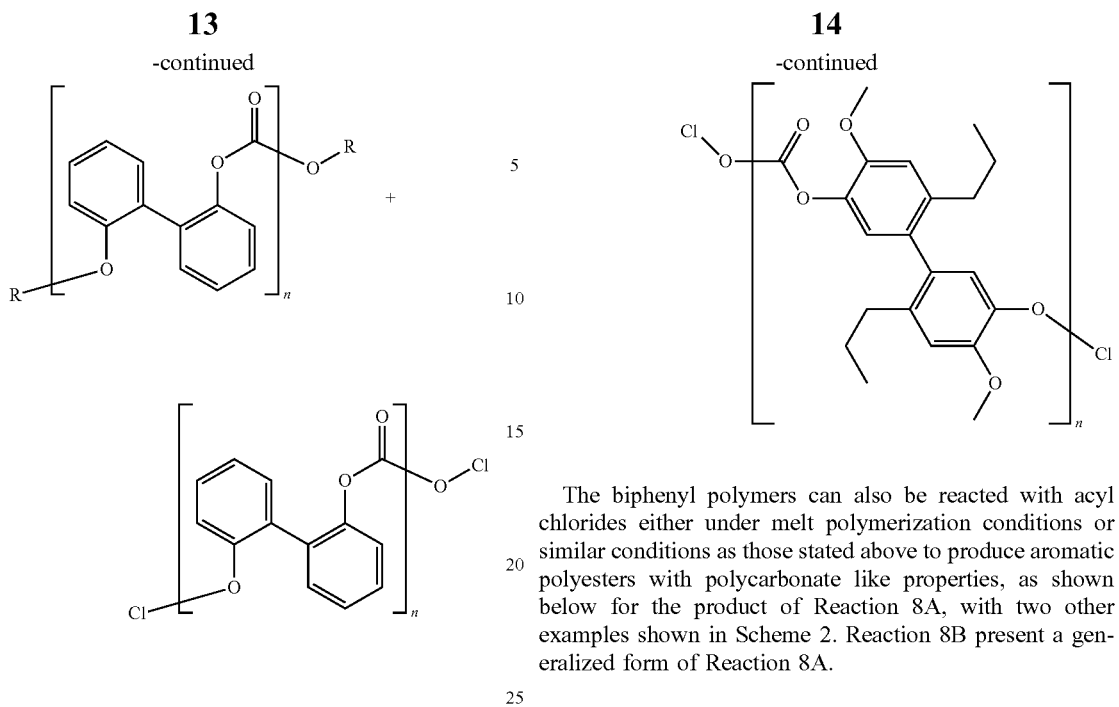
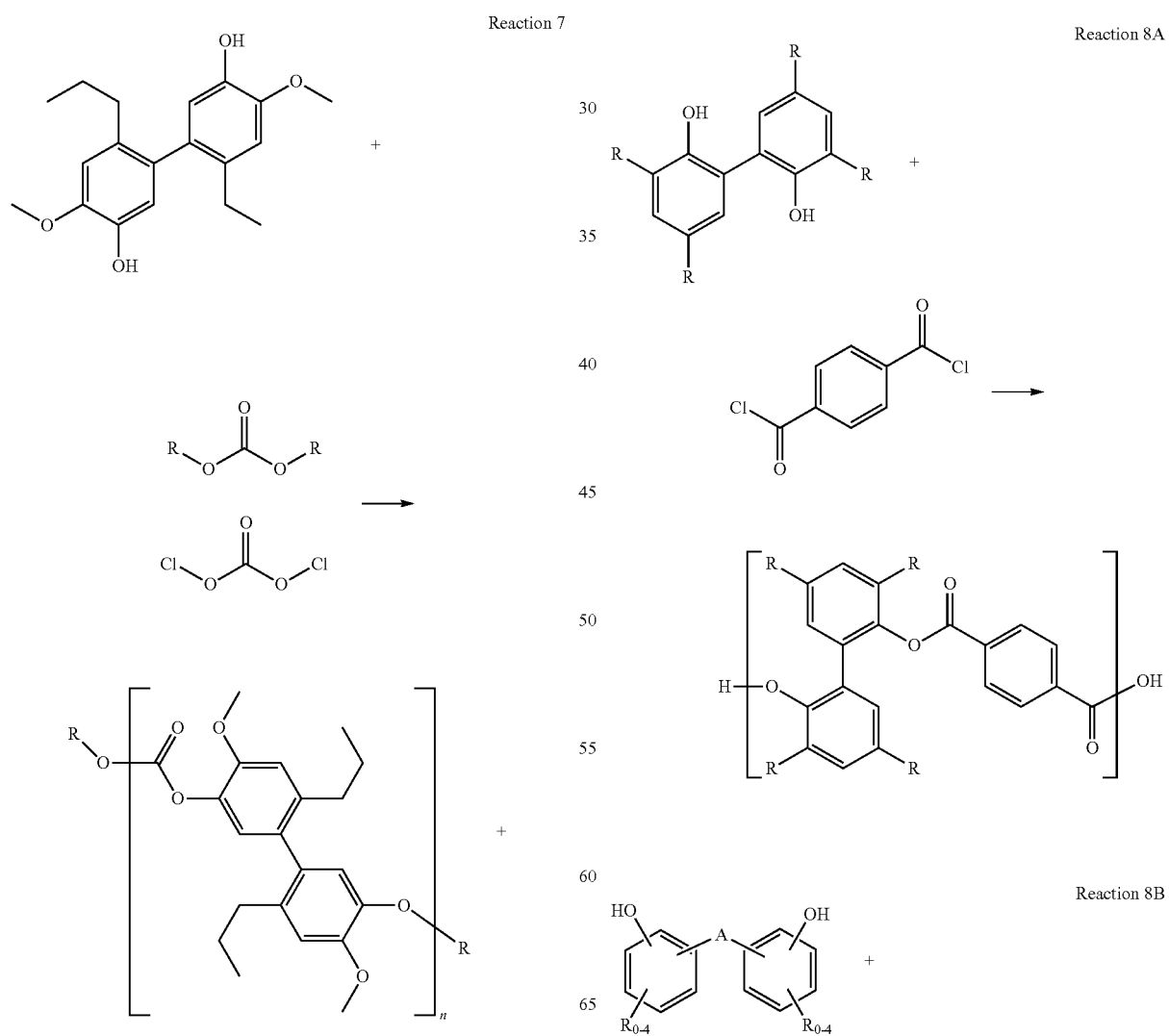
The biphenyl polymers can also be reacted with acyl chlorides either under melt polymerization conditions or similar conditions as those stated above to produce aromatic polyesters with polycarbonate like properties, as shown below for the product of Reaction 8A, with two other examples shown in Scheme 2. Reaction 8B present a generalized form of Reaction 8A.

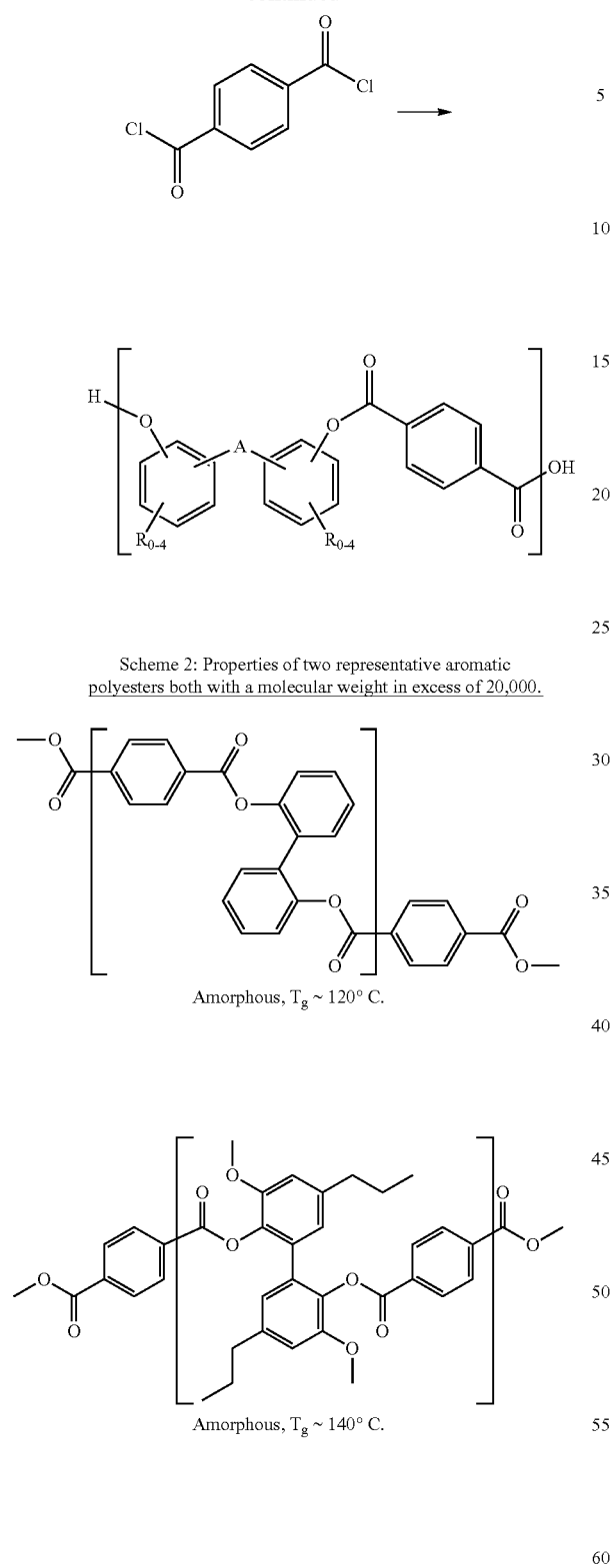

Scheme 2: Properties of two representative aromatic polyesters both with a molecular weight in excess of 20,000.

Amorphous, $T_g \sim 120°$ C.

Amorphous, $T_g \sim 140°$ C.

The products of Reactions 5-7 may be reduced to the generalized composition of Structure 6 shown above. Additional homopolymers that fall within the scope of the present disclosure, based on the biphenyl diols summarized in Scheme 1 are listed in Scheme 3 below.

Scheme 3: Bioderived Polycarbonate Replacement Homopolymers

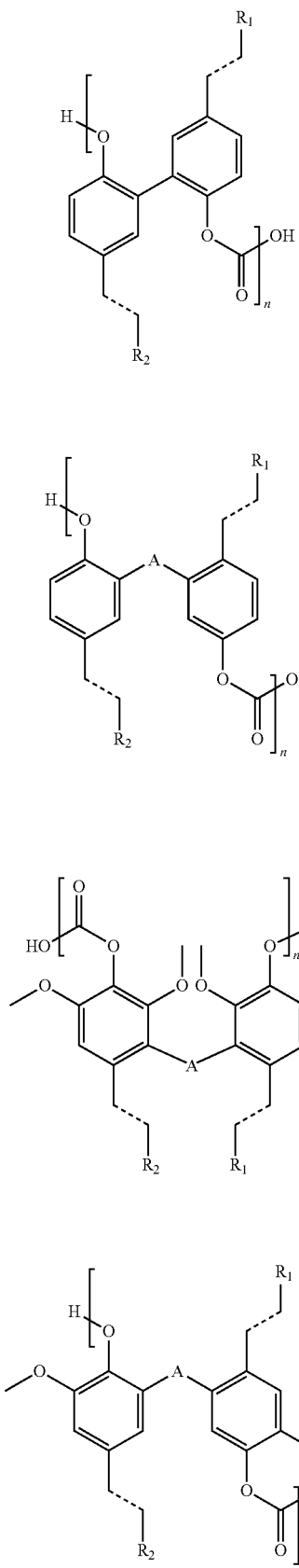

-continued

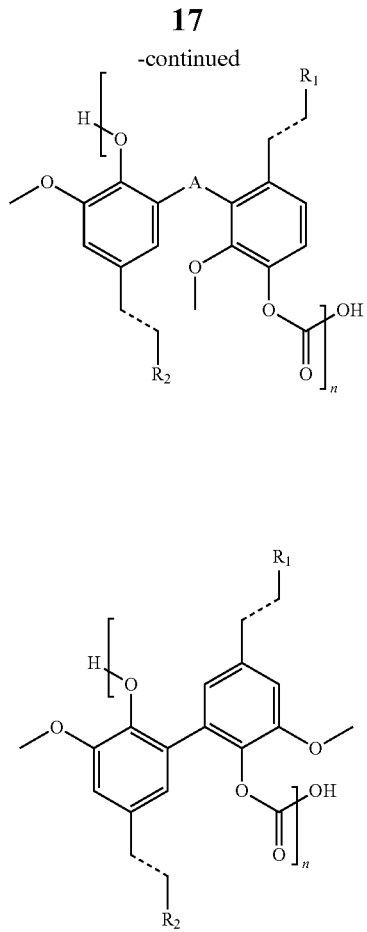

-continued

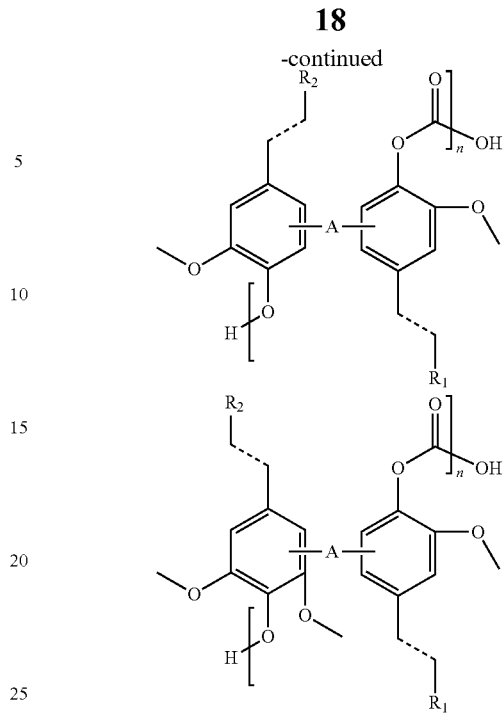

Figure 4:
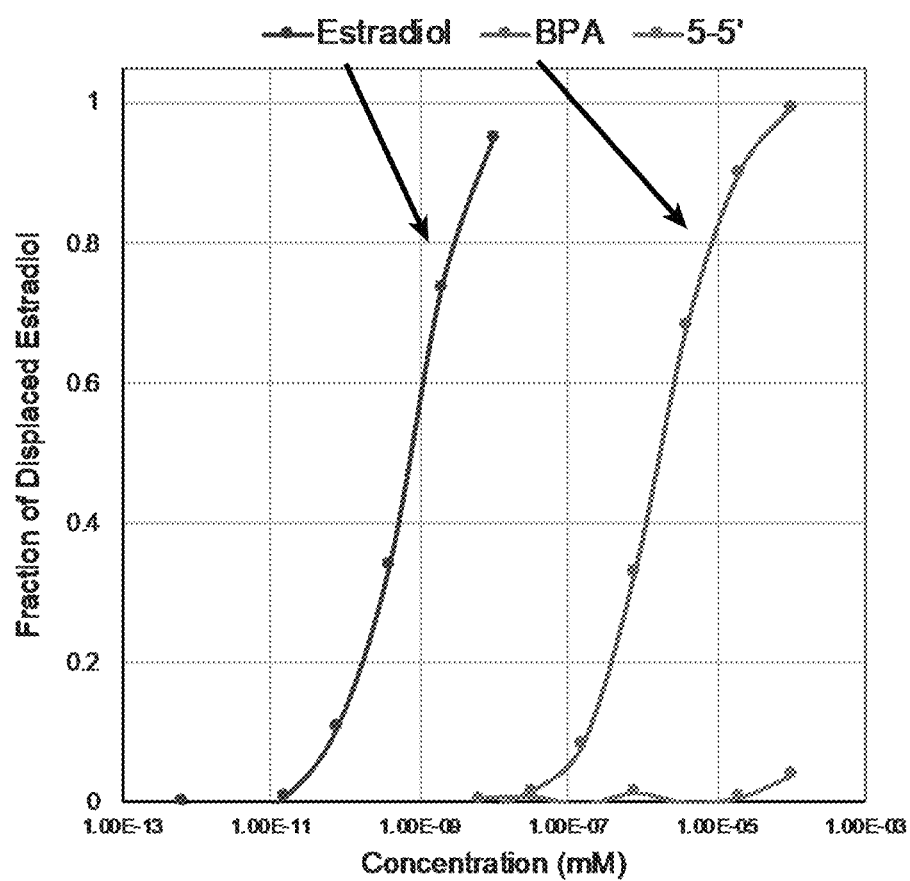
FIG. 4 illustrates binding/displacement data for the endocrine enzyme estradiol, according to some embodiments of the present disclosure.

The homopolymers resulting from the polymerization shown in Reaction 7 above, by the reaction of Structure 4 with at least one of a carbonate and/or halogenated carbonyl, have demonstrated significantly improved performance metrics compared to homopolymers that use BPA, resulting from the equivalent polymerization shown in Reaction 3 above, in particular regarding important health metrics. FIG. 4 demonstrates binding/displacement data for the endocrine enzyme estradiol. Dataset "E2" shows the concentrations needed of given molecule to displace a "nuclear labeled" estradiol. At a concentration of about 1E-09 mM nearly all of the labeled estradiol is displaced by estradiol. The "BPA" dataset shows that a 50,000 times higher concentration of BPA is required to displace essentially all of the originally bound labeled estradiol. However, unlike BPA, the dataset for Structure 4, labeled "5-5'", shows essentially zero displacement of estradiol over the same concentration range used for BPA. These data suggest that plastics and/or polymers manufactured using Structure 4, synthesized by Reaction 7, for example, may not have the same health issues as exhibited by BPA leaching from plastics containing BPA.

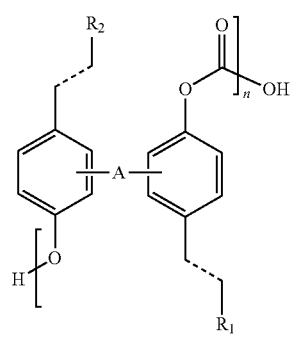

The generalized macromonomer shown in Reaction 1 may be further reacted, as described above, to form a polymer having the general structure shown below (Structure 7) (the R group may be an alcohol or an ester):

Structure 7

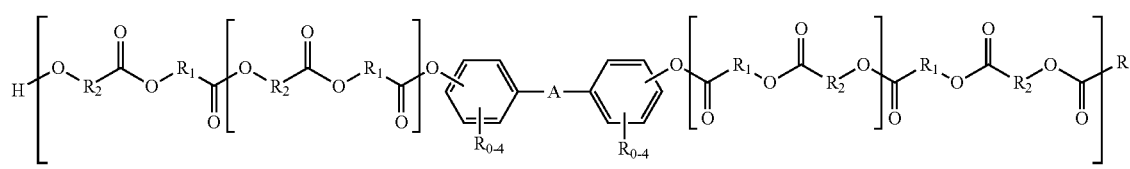

Structure 7 may now be thermally recycled in the same manner as the macromonomers shown in Reactions 1 and 2 above. Depending on lactide unit length (m and n in Structure 4) the polycarbonate may have the requisite thermal properties needed for satisfactory polycarbonate performance, specifically amorphous polymers with a higher glass-transition temperature (Tg). The specific polymer structure resulting from the macromonomer of Reaction 2 is shown below (Structure 8) with its corresponding thermal properties summarized in Table 2 below.

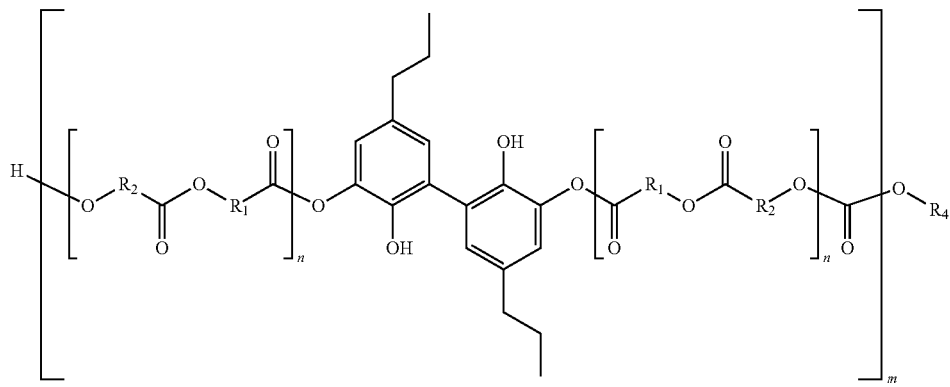

Structure 8

TABLE 2

| Tg as a function of lactide loading* | | |
|---|---|---|
| Lactide Loading, n | Tg | Amorphous |
| 0 | 110 | Yes |
| 1 | 120 | Yes |
| 10 | 70 | Yes |

*residual unmodified monomer may lead to slightly higher Tg

The modified lactone of Structure 5 can be polymerized by Reactions 1-3 to produce Structure 9 with control over the lactones with the requisite polycarbonate properties.

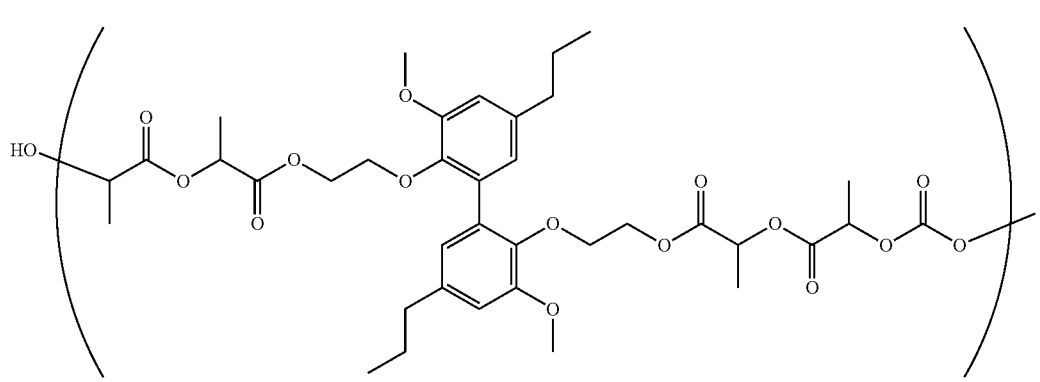

Structure 9

Clear, Amorphous, $T_g \sim 95°$ C.

Example Set 1

Example 1. A composition comprising:

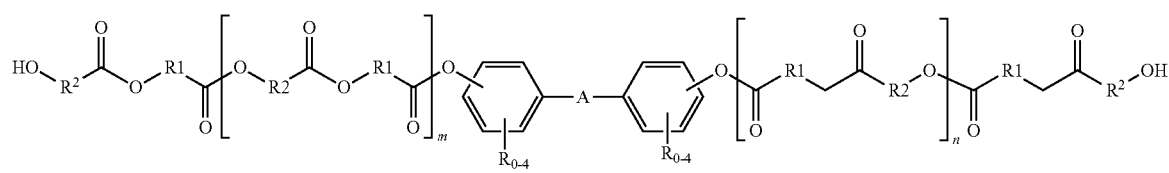

wherein: A comprises at least one of a carbon-carbon bond or a bridging group, R comprises between 0 and 4 of a first hydrocarbon, $R_1$ comprises a second hydrocarbon, $R_2$ comprises a third hydrocarbon, n is between 2 and 3,000, and m is between 2 and 3,000.

Example 2. The composition of Example 1, wherein the bridging group comprises a linear hydrocarbon chain or a branched hydrocarbon chain.

Example 3. The composition of Example 2, wherein the bridging group comprises between 1 and 10 carbon atoms.

Example 4. The composition of Example 1, wherein the bridging group is saturated.

Example 5. The composition of Example 1, wherein the bridging group is unsaturated.

Example 6. The composition of Example 1, wherein the bridging group further comprises at least one of an oxygen atom, a sulfur atom, a nitrogen atom, or a phosphorus atom.

Example 7. The composition of Example 1, wherein the bridging group further comprises at least one of an alcohol, a carboxylic acid, a methoxy group, an ether, or a furan.

Example 8. The composition of Example 1, wherein the R comprises a linear hydrocarbon chain or a branched hydrocarbon chain.

Example 9. The composition of Example 8, wherein R comprises between 1 and 10 carbon atoms.

Example 10. The composition of Example 1, wherein R is saturated.

Example 11. The composition of Example 1, wherein R is unsaturated.

Example 12. The composition of Example 1, wherein R further comprises at least one of an oxygen atom, a sulfur atom, a nitrogen atom, or a phosphorus atom.

Example 13. The composition of Example 1, wherein R further comprises at least one of an alcohol, a carboxylic acid, a methoxy group, an ether, an aromatic, or a furan.

Example 14. The composition of Example 1, wherein the $R_1$ comprises a linear hydrocarbon chain or a branched hydrocarbon chain.

Example 15. The composition of Example 14, wherein $R_1$ comprises between 1 and 10 carbon atoms.

Example 16. The composition of Example 1, wherein $R_1$ is saturated.

Example 17. The composition of Example 1, wherein $R_1$ is unsaturated.

Example 18. The composition of Example 1, wherein $R_1$ further comprises at least one of an oxygen atom, a sulfur atom, a nitrogen atom, or a phosphorus atom.

Example 19. The composition of Example 1, wherein $R_1$ further comprises at least one of an alcohol, a carboxylic acid, a methoxy group, an ether, an aromatic, or a furan.

Example 20. The composition of Example 1, wherein the $R_2$ comprises a linear hydrocarbon chain or a branched hydrocarbon chain.

Example 21. The composition of Example 20, wherein $R_2$ comprises between 1 and 10 carbon atoms.

Example 22. The composition of Example 1, wherein $R_2$ is saturated.

Example 23. The composition of Example 1, wherein $R_2$ is unsaturated.

Example 24. The composition of Example 1, wherein $R_2$ further comprises at least one of an oxygen atom, a sulfur atom, a nitrogen atom, or a phosphorus atom.

Example 25. The composition of Example 1, wherein $R_2$ further comprises at least one of an alcohol, a carboxylic acid, a methoxy group, an ether, an aromatic, or a furan.

Example 26. The composition of Example 1, wherein A and R are derived from a biphenyl diol.

Example 27. The composition of Example 26, wherein the biphenyl diol is bioderived.

Example Set 2

Example 1. A composition comprising:

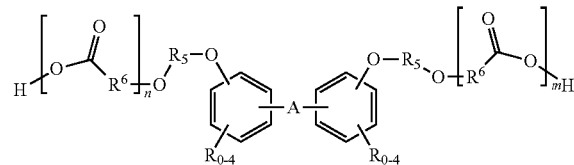

wherein: A comprises at least one of a carbon-carbon bond or a bridging group, R comprises between 0 and 4 of a first hydrocarbon, $R_5$ comprises a second hydrocarbon, $R_6$ comprises a third hydrocarbon, n is between 2 and 2,000, and m is between 2 and 2,000.

Example 2. The composition of Example 1, wherein the bridging group comprises a linear hydrocarbon chain or a branched hydrocarbon chain.

Example 3. The composition of Example 2, wherein the bridging group comprises between 1 and 10 carbon atoms.

Example 4. The composition of Example 1, wherein the bridging group is saturated.

Example 5. The composition of Example 1, wherein the bridging group is unsaturated.

Example 6. The composition of Example 1, wherein the bridging group further comprises at least one of an oxygen atom, a sulfur atom, a nitrogen atom, or a phosphorus atom.

Example 7. The composition of Example 1, wherein the bridging group further comprises at least one of an alcohol, a carboxylic acid, a methoxy group, an ether, or a furan.

Example 8. The composition of Example 1, wherein the R comprises a linear hydrocarbon chain or a branched hydrocarbon chain.

Example 9. The composition of Example 8, wherein R comprises between 1 and 10 carbon atoms.

Example 10. The composition of Example 1, wherein R is saturated.

Example 11. The composition of Example 1, wherein R is unsaturated.

Example 12. The composition of Example 1, wherein R further comprises at least one of an oxygen atom, a sulfur atom, a nitrogen atom, or a phosphorus atom.

Example 13. The composition of Example 1, wherein R further comprises at least one of an alcohol, a carboxylic acid, a methoxy group, an ether, an aromatic, or a furan.

Example 14. The composition of Example 1, wherein the $R_5$ comprises a linear hydrocarbon chain or a branched hydrocarbon chain.

Example 15. The composition of Example 14, wherein $R_5$ comprises between 1 and 10 carbon atoms.

Example 16. The composition of Example 1, wherein $R_5$ is saturated.

Example 17. The composition of Example 1, wherein $R_5$ is unsaturated.

Example 18. The composition of Example 1, wherein $R_5$ further comprises at least one of an oxygen atom, a sulfur atom, a nitrogen atom, or a phosphorus atom.

Example 19. The composition of Example 1, wherein $R_5$ further comprises at least one of an alcohol, a carboxylic acid, a methoxy group, an ether, an aromatic, or a furan.

Example 20. The composition of Example 1, wherein the $R_6$ comprises a linear hydrocarbon chain or a branched hydrocarbon chain.

Example 21. The composition of Example 20, wherein $R_6$ comprises between 1 and 10 carbon atoms.

Example 22. The composition of Example 1, wherein $R_6$ is saturated.

Example 23. The composition of Example 1, wherein $R_6$ is unsaturated.

Example 24. The composition of Example 1, wherein $R_6$ further comprises at least one of an oxygen atom, a sulfur atom, a nitrogen atom, or a phosphorus atom.

Example 25. The composition of Example 1, wherein $R_6$ further comprises at least one of an alcohol, a carboxylic acid, a methoxy group, an ether, an aromatic, or a furan.

Example 26. The composition of Example 1, wherein A and R are derived from a biphenyl diol.

Example 27. The composition of Example 1, wherein $R_5$ and $R_6$ are derived from a lactone.

Example 28. The composition of Example 26, wherein the biphenyl diol is bioderived.

Example Set 3

Example 1. A composition comprising:

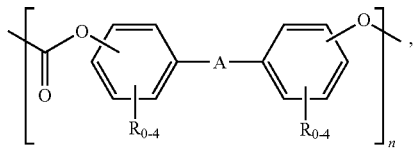

wherein: A comprises at least one of a carbon-carbon bond or a bridging group, R comprises between 0 and 4 of a first hydrocarbon, and n is between 2 and 3,000.

Example 2. The composition of Example 1, wherein the bridging group comprises a linear hydrocarbon chain or a branched hydrocarbon chain.

Example 3. The composition of Example 2, wherein the bridging group comprises between 1 and 10 carbon atoms.

Example 4. The composition of Example 1, wherein the bridging group is saturated.

Example 5. The composition of Example 1, wherein the bridging group is unsaturated.

Example 6. The composition of Example 1, wherein the bridging group further comprises at least one of an oxygen atom, a sulfur atom, a nitrogen atom, or a phosphorus atom.

Example 7. The composition of Example 1, wherein the bridging group further comprises at least one of an alcohol, a carboxylic acid, a methoxy group, an ether, or a furan.

Example 8. The composition of Example 1, wherein the R comprises a linear hydrocarbon chain or a branched hydrocarbon chain.

Example 9. The composition of Example 8, wherein R comprises between 1 and 10 carbon atoms.

Example 10. The composition of Example 1, wherein R is saturated.

Example 11. The composition of Example 1, wherein R is unsaturated.

Example 12. The composition of Example 1, wherein R further comprises at least one of an oxygen atom, a sulfur atom, a nitrogen atom, or a phosphorus atom.

Example 13. The composition of Example 1, wherein R further comprises at least one of an alcohol, a carboxylic acid, a methoxy group, an ether, an aromatic, or a furan.

Example 14. The composition of Example 1, wherein A and R are derived from a biphenyl diol.

Example 15. The composition of Example 14, wherein the biphenyl diol is bioderived.

Example Set 4

Example 1. A composition comprising:

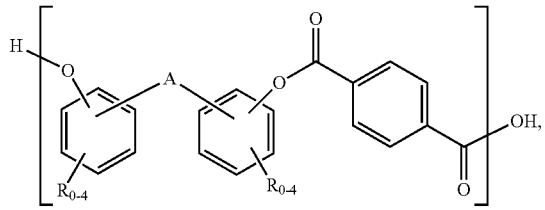

wherein: A comprises at least one of a carbon-carbon bond or a bridging group, R comprises between 0 and 4 of a first hydrocarbon, and n is between 2 and 3,000.

Example 2. The composition of Example 1, wherein the bridging group comprises a linear hydrocarbon chain or a branched hydrocarbon chain.

Example 3. The composition of Example 2, wherein the bridging group comprises between 1 and 10 carbon atoms.

Example 4. The composition of Example 1, wherein the bridging group is saturated.

Example 5. The composition of Example 1, wherein the bridging group is unsaturated.

Example 6. The composition of Example 1, wherein the bridging group further comprises at least one of an oxygen atom, a sulfur atom, a nitrogen atom, or a phosphorus atom.

Example 7. The composition of Example 1, wherein the bridging group further comprises at least one of an alcohol, a carboxylic acid, a methoxy group, an ether, or a furan.

Example 8. The composition of Example 1, wherein the R comprises a linear hydrocarbon chain or a branched hydrocarbon chain.

Example 9. The composition of Example 8, wherein R comprises between 1 and 10 carbon atoms.

Example 10. The composition of Example 1, wherein R is saturated.

Example 11. The composition of Example 1, wherein R is unsaturated.

Example 12. The composition of Example 1, wherein R further comprises at least one of an oxygen atom, a sulfur atom, a nitrogen atom, or a phosphorus atom.

Example 13. The composition of Example 1, wherein R further comprises at least one of an alcohol, a carboxylic acid, a methoxy group, an ether, an aromatic, or a furan.

Example 14. The composition of Example 1, wherein A and R are derived from a biphenyl diol.

Example 15. The composition of Example 14, wherein the biphenyl diol is bioderived.

Example Set 5

Example 1. A method comprising: reacting

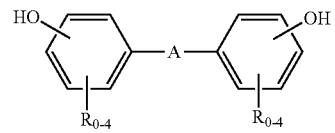

with

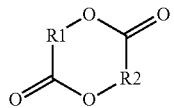

to produce

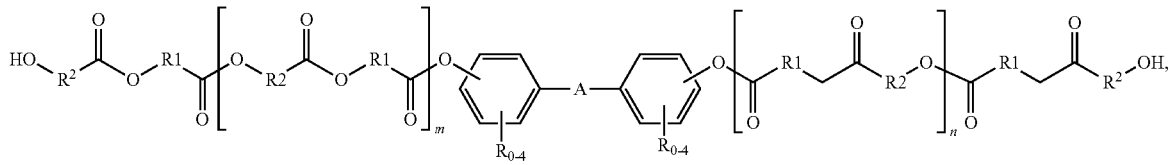

wherein: A comprises at least one of a carbon-carbon bond or a bridging group, R comprises between 0 and 4 of a first hydrocarbon, $R_1$ comprises a second hydrocarbon, $R_2$ comprises a third hydrocarbon, n is between 1 and 500, and m is between 1 and 500.

Example 2. A method comprising: a first reacting of

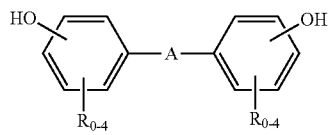

with

to produce a first product having a first structure comprising

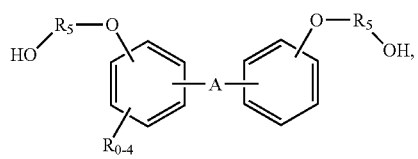

wherein: A comprises at least one of a carbon-carbon bond or a bridging group, R comprises between 0 and 4 of a first hydrocarbon, and $R_5$ comprises a second hydrocarbon.

Example 3. The method of Example 2, further comprising: a second reacting of the first product and

to produce a second product having a second structure comprising

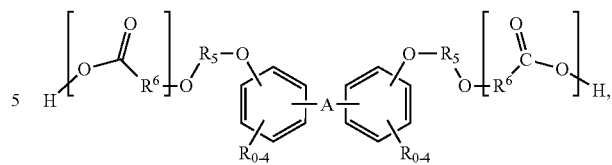

wherein $R_6$ comprises a third hydrocarbon.

Example 4. A method comprising: reacting

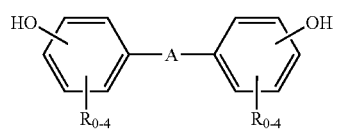

with at least one of a carbonate or a halogenated carbonyl to produce

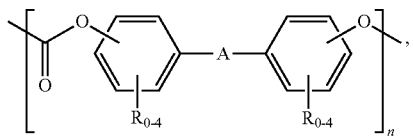

wherein: A comprises at least one of a carbon-carbon bond or a bridging group, R comprises between 0 and 4 of a first hydrocarbon, and n is between 1 and 500.

Example 5. A method comprising: reacting

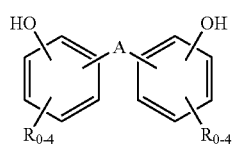

with

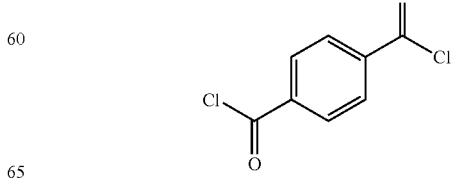

to produce

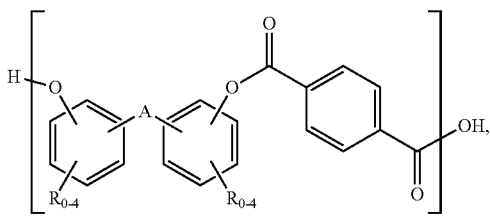

wherein: A comprises at least one of a carbon-carbon bond or a bridging group, R comprises between 0 and 4 of a first hydrocarbon, and n is between 1 and 500.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:

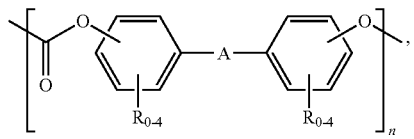

wherein:
A comprises at least one of a carbon-carbon bond or a bridging group,
R comprises between 0 and 4 of a first hydrocarbon, the first hydrocarbon comprises a linear hydrocarbon chain or a branched hydrocarbon chain, and
n is between 2 and 3,000.

2. The composition of claim 1, wherein the bridging group comprises a linear hydrocarbon chain or a branched hydrocarbon chain.

3. The composition of claim 2, wherein the bridging group comprises between 1 and 10 carbon atoms.

4. The composition of claim 1, wherein the bridging group is saturated.

5. The composition of claim 1, wherein the bridging group is unsaturated.

6. The composition of claim 1, wherein the bridging group further comprises at least one of an oxygen atom, a sulfur atom, a nitrogen atom, or a phosphorus atom.

7. The composition of claim 1, wherein the bridging group further comprises at least one of an alcohol, a carboxylic acid, a methoxy group, an ether, or a furan.

8. The composition of claim 1, wherein R comprises between 1 and 10 carbon atoms.

9. The composition of claim 1, wherein R is saturated.

10. The composition of claim 1, wherein R is unsaturated.

11. The composition of claim 1, wherein R further comprises at least one of an oxygen atom, a sulfur atom, a nitrogen atom, or a phosphorus atom.

12. The composition of claim 1, wherein R further comprises at least one of an alcohol, a carboxylic acid, a methoxy group, an ether, an aromatic, or a furan.

13. The composition of claim 1, wherein A and R are derived from a biphenyl diol.

14. The composition of claim 13, wherein the biphenyl diol is bioderived.

15. A composition comprising:

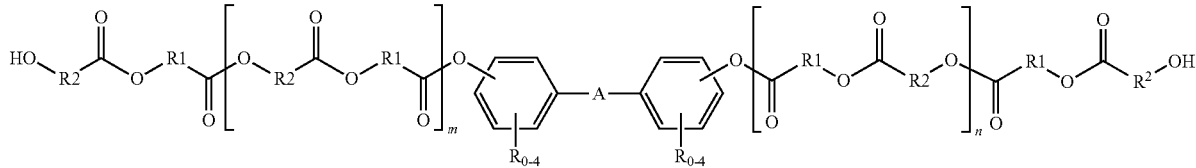

wherein:
A comprises at least one of a carbon-carbon bond or a bridging group,
R comprises between 0 and 4 of a first hydrocarbon,
the first hydrocarbon comprises a linear hydrocarbon chain or a branched hydrocarbon chain,
$R_1$ comprises a second hydrocarbon,
$R_2$ comprises a third hydrocarbon,
n is between 2 and 3,000, and
m is between 2 and 3,000.

16. A composition comprising:

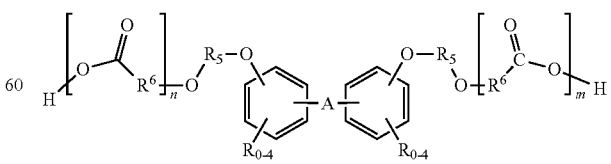

wherein:
A comprises at least one of a carbon-carbon bond or a bridging group,

R comprises between 0 and 4 of a first hydrocarbon,
the first hydrocarbon comprises a linear hydrocarbon chain or a branched hydrocarbon chain,
$R_5$ comprises a second hydrocarbon,
$R_6$ comprises a third hydrocarbon,
n is between 2 and 2,000, and
m is between 2 and 2,000.

17. A composition comprising:

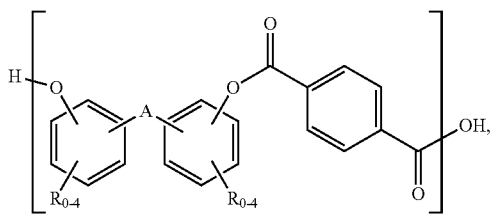

wherein:
A comprises at least one of a carbon-carbon bond or a bridging group,
R comprises between 0 and 4 of a first hydrocarbon,
the first hydrocarbon comprises a linear hydrocarbon chain or a branched hydrocarbon chain, and
n is between 2 and 3,000.

18. A method comprising:
a first reacting of

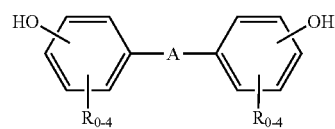

with

to produce a first product having a first structure comprising

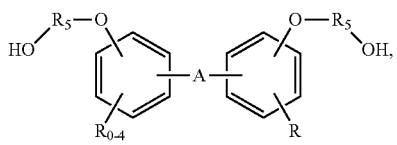

wherein:
A comprises at least one of a carbon-carbon bond or a bridging group,
R comprises between 0 and 4 of a first hydrocarbon,
the first hydrocarbon comprises a linear hydrocarbon chain or a branched hydrocarbon chain, and
$R_5$ comprises a second hydrocarbon.

19. The method of claim 18, further comprising:
a second reacting of the first product and

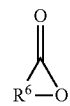

to produce a second product having a second structure comprising

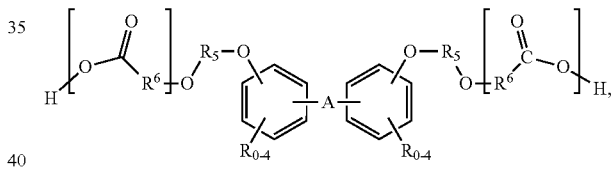

wherein $R_6$ comprises a third hydrocarbon.

* * * * *